(12) United States Patent
Machin

(10) Patent No.: US 9,074,191 B2
(45) Date of Patent: Jul. 7, 2015

(54) METHODS AND SYSTEMS FOR PRODUCING LIPIDS FROM MICROALGAE USING CULTURED MULTI-SPECIES MICROALGAE

(76) Inventor: Marcelo Gonzalez Machin, Puerto Madryn (AR)

( * ) Notice: Subject to any disclaimer, the term of this patent is extended or adjusted under 35 U.S.C. 154(b) by 149 days.

(21) Appl. No.: 12/982,096

(22) Filed: Dec. 30, 2010

(65) Prior Publication Data

US 2011/0294196 A1    Dec. 1, 2011

Related U.S. Application Data

(60) Provisional application No. 61/291,337, filed on Dec. 30, 2009, provisional application No. 61/291,344, filed on Dec. 30, 2009.

(51) Int. Cl.
*C12N 1/12* (2006.01)
*C12M 1/00* (2006.01)
*C12P 7/64* (2006.01)

(52) U.S. Cl.
CPC .............. *C12N 1/12* (2013.01); *C12P 7/6463* (2013.01); *C12M 21/02* (2013.01); *C12M 23/02* (2013.01); *C12M 23/18* (2013.01); *C12M 23/38* (2013.01)

(58) Field of Classification Search
None
See application file for complete search history.

(56) References Cited

U.S. PATENT DOCUMENTS

2010/0050502 A1\* 3/2010 Wu et al. .................... 44/308
2012/0231513 A1\* 9/2012 Stephen et al. ............. 435/134

\* cited by examiner

*Primary Examiner* — Cherie M Stanfield
*Assistant Examiner* — Paul D. Pyla
(74) *Attorney, Agent, or Firm* — Ladas & Parry LLP

(57) ABSTRACT

The present invention provides a system and method for culturing a microalgae biofamily to produce lipids. The method includes growing a microalgae biofamily comprises multiple microalgae species in a liquid medium at a first stress level. A portion of the microalgae are exposed to a second stress level and harvested. Lipids are extracted from the harvested portion. Also disclosed is a system for culturing a microalgae biofamily that comprises an enclosed pond containing microalgae in growth medium and having a sloped bottom, at least one photobioreactor positioned above the pond, and a pump circulating the microalgae-containing growth medium between the pond and the at least one photobioreactor.

7 Claims, 4 Drawing Sheets

METHODS AND SYSTEMS FOR PRODUCING LIPIDS FROM MICROALGAE USING CULTURED MULTI-SPECIES MICROALGAE

RELATED APPLICATIONS

This application claims priority to and the benefit of U.S. Provisional Patent Application Ser. Nos. 61/291,337, filed Dec. 30, 2009, and 61/291,344, also filed Dec. 30, 2009, the texts of which are incorporated herein by reference in their entirety.

FIELD OF THE INVENTION

In general, the present invention relates to oil production using microalgae. In particular, various embodiments relate to microalgae biofamilies that include multiple algae species, and to systems and methods for algae culturing and harvesting as well as oil extraction.

BACKGROUND

Microalgae cultures are an alternative, renewable source of oil. Research and development efforts in recent years have been directed to optimizing both the microalgae cultures themselves, and the systems and methods used for farming and processing them, with the goal of achieving large-scale, commercial deployment of microalgae oil production. Most algae farms select a microalgae species of desirable robustness, growth rate, and oil yield, and grow an algae monoculture in open ponds, closed ponds, or bioreactors. Each of these approaches has advantages and drawbacks.

Open ponds can be categorized as either natural waters (lakes, lagoons, ponds) or artificial ponds or containers. Most systems utilize large shallow ponds, tanks, circular ponds, or raceway ponds. Open ponds are typically easier to construct and operate than most closed systems, and thus provide significant capital and operation cost advantages. However, they have a large footprint (in particular, compared with photobioreactors), and their biomass productivity and efficiency are often limited by uneven light distribution in the pond and poor light utilization by the cells, evaporative losses, diffusion of $CO_2$ to the atmosphere, and low mass transfer rates due to insufficient stirring mechanisms. Further, contamination by predators and other fast-growing heterotrophs have restricted the commercial production of microalgae in open culture systems to only those organisms that can withstand such intruders. In addition, open ponds allow little or no control over the temperature and other environmental conditions in and around the pond. As a result, the water temperature at which the production levels are maximized can be difficult to maintain, and weather conditions can stunt algae growth. The geographic regions deemed most suitable for such algae culture systems have been warm, tropical or dry climate zones (e.g., Israel, Brazil, Arizona, Hawaii).

Closed ponds combine open ponds with a translucent cover (e.g., made of plexiglass), which forms a greenhouse above the pond and facilitates greater control over the environment. This can eliminate many of the problems associated with an open system. It may allow the species that are being grown to stay dominant, extend the growing season, and facilitate optimal year-round production if the greenhouse is temperature-controlled. Further, the amount of carbon dioxide may be increased in these quasi-closed systems, which, in turn, increases the algae growth rate. On the downside, closed pond systems cost more than the open ponds, which usually results in a smaller system. Closed ponds are commonly used for commercial spirulina cultivation.

Algae can also be grown in a photobioreactor (PBR), e.g., a closed bioreactor which facilitates exposure of the microorganisms contained therein to light, for example, by being translucent or by incorporating an artificial light source. PBRs are typically more complex than open or closed ponds. Like closed ponds, PBRs allow the cultured species to stay dominant and extend the growing season slightly if unheated and to a full year if heated, but generally require significant cooling energy, especially in warm climates. Because PBRs are closed, all essential nutrients need to be artificially introduced into the system to allow algae growth. A PBR may be operated in "batch mode." Alternatively, a continuous stream of sterilized water, containing nutrients, air, and carbon dioxide, may be introduced, and algae may be harvested as they grow and cause excess culture to overflow. Once a continuous PBR is successfully started, it can continue to operate for long periods. However, if sufficient care is not taken, continuous bioreactors can easily collapse. An advantage of continuous PBRs that harvest algae are generally in the "log phase," containing higher nutrient content than old "senescent" algae. The maximum productivity for a bioreactor occurs when the "exchange rate" (i.e., the time to exchange one volume of liquid) is equal to the "doubling time" (e.g., in mass or volume) of the algae. To increase the commercial viability of oil production with microalgae, it is desirable to increase the oil production and overall efficiency of microalgae culture systems and facilitate microalgae growth under a wider range of environmental conditions.

SUMMARY

The present invention provides microalgae cultures that can (i) proliferate in colder climates (e.g., in non-tropical climates) as well as warmer climates, (ii) possess improved resistance to predator species, bacteria, and viruses and/or robustness to culture collapse, and/or (iii) produce oil of higher quality or in larger quantities than conventional microalgae cultures. Further, the invention provides systems and methods for facilitating high algae growth rates, triggering increased lipid production, and harvesting algae and extracting oil at lower energy cost and water consumption than previous methods and is specifically robust to be able to minimize resource use regardless of ambient operating environment.

In contrast to prior-art microalgae systems that use monocultures or organisms that are highly selected for oil content and/or growth rate, cultures in accordance with embodiments of the present invention include multiple microalgae species that form a biofamily with symbiotic relations and interdependencies among the various species. The establishment of interdependent species is a basis of certain embodiments of the invention. In many respects, the biofamily may emulate microalgae collections as they occur in nature. However, in embodiments of this invention, microalgae are isolated from other organisms for farming, and often (but not necessarily) grown in conditions different from their natural environment. For example, the biofamily may include cold-water microalgae isolated from ocean depths of 3 meters or more, which, when cultured in different temperature, light, nutrient and salinity, grow faster and/or produce more lipids and/or different lipid chains, than their counterparts in the ocean. In certain embodiments, the microalgae culture includes, as its two fundamental species, *Anabaena* sp. and *Nostoc* sp. Additional microalgae species may be added to the collection to enhance its defensive and productive characteristics. The biofamily may, for example, include at least five, at least ten, at least twelve, or at least eighteen different species.

Systems for microalgae culture in accordance with various embodiments may include both a pond and one or more photobioreactors, thus using the advantages, and mitigating the disadvantages, of the two structures. In one embodiment, flat photobioreactors are arranged adjacent to (e.g., next to or above) a closed pond (e.g., on top of the roof of the pond), and microalgae are cycled through the pond and at least one photobioreactor. The system may, additionally, include one or more piping headers wherein microalgae reside and into which $CO_2$ is injected (hereinafter referred to as the $CO_2$ headers, $CO_2$ circuits, or simply headers). The $CO_2$ headers may serve as the central integration point of the system. Culture medium containing microalgae may flow between the pond/bioreactor subsystem and the $CO_2$ header(s). In some embodiments, the system includes two $CO_2$ headers. During the normal algae growth phase, the algae may be cycled multiple times a day between the pond/bioreactor subsystem and the first header, where they are supplied with $CO_2$ and nutrients. To harvest the algae, they may be conducted through a second header, where increased exposure to light and $CO_2$ may induce the conversion of some of their lipids into other, more desirable lipids. In certain embodiments, they algae stay in the second header for about 24 hours, and are then harvested through a harvest port on the return path from the second header.

The microalgae may be cultured in "brackish" water, e.g., water with a salinity between that of fresh water and that of seawater (e.g., a salinity of about 30% of the salinity of pure seawater to nearly fresh or sweet water). To optimize algae growth, recycled biomass, micronutrients, carbon dioxide, and/or oxygen may be introduced into the system at a desired rate, and temperature, pH level, and lighting conditions may be controlled. Harvesting may involve inducing algae gelling, e.g., injecting chilled carbon dioxide into the liquid medium. The cell walls may then be ruptured using a supercritical-$CO_2$ process, which may be more energy-efficient as a result of the gelification of algae. After separation of the oil from the plant matter, the oil may be refined to produce, e.g., biodiesel or other biofuels, biochemicals, nutritional compounds and other useful and valuable products that can be produced from pure algae oils and biomass.

In one aspect, the invention provides an isolated symbiotic microalgae biofamily including at least two foundational microalgae species, *Anabaena* sp. and *Nostoc* sp., the combination of which confers resistance to predatory algae, bacteria, and/or viral infection. In some embodiments, at least one of the microalgae species is a deep water algae species that may be isolated from water depths of at least 3 meters and water temperatures from −4 to 20 degrees C.

The biofamily may include cyanobacteria, autotrophic microalgae, heterotrophic microalgae, and eukaryotic microalgae. In certain embodiments, the biofamily may include two or more species selected from the group consisting of *Euglena* sp. (*gracilis*), *Anabaena* sp. (e.g., *Anabaena variabilis, cylindrica, hassali,* and/or *planctonica*) and/or mutants thereof (e.g., AnaPat 368, AnaPat485, AnaPat324), AaronPat099 and/or AaronPat 0997, Biejclinc 4222, *Achananthes orientalis, Amphora* (e.g., *Amphora delicatissima* or *cafeiformis*), *Ankistnodesmus falcatus, Calothrix* (e.g., *Calothrix confervicola* and/or *crustacea*), *Chaetoceros* sp. (e.g., *Chaetoceros muelleri, gracilis,* and/or *muelleri subsalsum*), *Chaetomorpha linum, Clorococcum* sp., *Chlorrella* sp. (e.g., *Chlorrella ellipsoidea, Chlorrella pyrenoidosa,* and/or *Chlorrella salina*), *Chromonas* sp., *Chroococcus Turgidus, Chrysosphaera* sp., *Coelastrum* sp., *Calothrix crustacea, Cricophaera* sp., *Cryptomonas* sp., *Cyclotella* sp. (e.g., *Cyclotella meneghiniana* and/or *cryptica*), *Dermocarpa olivaceus, Dunaliella* sp. (e.g., *Dunaliella salina, bardawil,* and/or *tertioleta*), *Euglena viridis,* Fabilez 0093, *Navicula* sp. *Amphiprora hyalina, Eustigmatophyte flagellate, Pleuorochysis* sp., *Franceia* sp., *Gleocapsa* sp., *Gloeothamnion* sp., *Hydrocoleum* (e.g., *Hydrocoleum lyngbyaceium* and/or *holdenii*), *Hymenomonas* sp., *Isochrysis* aff. *Galbana, Microcoleus chthonoplastes, Microcoleus tenerrimus, Monoraphidium* sp., *Nannochloropsis* sp. (e.g., *Nannochloropsis salina*), *Navicula* (e.g., *Navicula saprophil, pseudotenelloides, biskanterae, acceptata, saprophila,* and/or *pseudotenelloides*), *Nephrochloris* sp., *Nitzschia* sp. (e.g., *Nitzschia pusilla monoensis, elliptica, alexandrina, quadrangula, pusila monoensis, inconspicua, microcephala, frustulum, hantzchianna, intermedia, frustulum,* and/or *communis*), *Nodularia harveyana, Nostoc* sp., *Ochromonas* sp., *Oocystis* sp. (e.g., *Oocystis pusilla*), *Oscillatoria* sp. (e.g., *corallinae, subborevis, limnetica,* and/or *limosa*), *Pediastrum* sp. (e.g., *Pediastrum clarthatum*), *Phaeodactylum tricomutum, Platymonas* sp., *Pleurochrysis* sp. (e.g., *Pleurochrysis dentate*), *Prymnesiophyte* sp., *Pseudoanabaena* sp., *Pyraminonas* sp., *Rivularia nitida, Schizothrix cacicota, Siderocelis* sp., *Spirulina* sp. (e.g., *Spirulina platensis* and/or *Spirulina maxima*), *Stichococcus* sp., *Synechococcus* sp., *Tetraselmis suecica, Thalassiosira weissflogii, Tolypothrix lanata, Volvox aurex,* and/or YagoPat 077 and/or YagoPat 079. In certain embodiments, the biofamily may include at least five, at least ten, at least twelve, or at least eighteen different species. For example, in an exemplary embodiment, the microalgae biofamily may include *Anabaena* sp., *Nostoc* sp. *Oscillatoria limosa, Tolypothrix lanata, Calothrix crustacea, Chroococcus* sp., *Coelastrum* sp., *Pediastrum* sp., *Siderocelis* sp., *Volvox aureux, Eucilena viriodis,* and *Microcoleus tenerrimus.*

In another aspect, the invention provides a method for building a microalgae biofamily including the steps of: (a) selecting at least two foundational microalgae species, *Anabaena* sp. and *Nostoc* sp.; (b) adding additional microalgae species that confer resistance to predator species, bacterial, and viruses; and (c) culturing the microalgae species selected in steps (a) and (b) in liquid medium. The method may include selecting at least one deep water algae species wherein the deep water algae species is adapted to grow at a first temperature, light intensity, salinity and nutrient source, but is cultured at a second temperature, light intensity, salinity and nutrient source. In some embodiments, the second light intensity may be at least ten-fold higher than the first light intensity. In other embodiments, the second temperature may be at least 5 degrees C. higher than the first temperature. Various micronutrients may be added to the microalgae culture in step (c) including $KNO_3$, $K_2HPO_4$, $CaCl_2$, $MgSO_4$, ferric citrate, citric acid, $CoCl_2$, $H_3BO_3$, $MnCl_2$, $ZnSO_4$, $CuSO_4$, $Na_2MoO_4$, various silica, nitrogen, phosphorous pentoxide, potassium oxide, magnesium oxide, sulfur trioxide, calcium oxide, boron, iron, and zinc. The microalgae biofamily may be cultured in an enclosed system including an enclosed pond, a photobioreactor, or a combination thereof, including circulation between the two that includes circulating the full volume of the pond through the photobioreactor several times per day, and circulation of the same to the $CO_2$ header for delivery of $CO_2$, nutrients and water chemistry adjustments.

In another aspect, the invention provides methods for microalgae lipid production. In some embodiments, the method includes growing a microalgae biofamily as described herein in a liquid medium at a first stress level; harvesting a portion of the microalgae; and extracting lipids from the harvested portion. In another embodiment, the method includes growing a microalgae biofamily comprising multiple microalgae species in a liquid medium at a first stress level, wherein at least one of the microalgae species is a deep-water algae species; harvesting a portion of the microalgae; and extracting lipids from the harvested portion. In other embodiments, the method includes growing a microalgae biofamily in a liquid medium at a first stress level, harvesting a portion of the microalgae by exposing the microalgae to a second stress level; and extracting lipids from the harvested portion. The liquid medium at a first stress level may contain nitrogen, ammonium, ammonium nitrate, ammonium acetate, and calcium carbonate. In some embodiments, the liquid medium is water having a salinity of between about 1% and about 50% of the salinity of seawater. The liquid medium may be maintained between a pH of 6.5 to 8.5 and/or may have a CO2 concentration of 0.8 kg/kg biomass.

In some embodiments, the microalgae are harvested at an algae concentration equal to or above 36 g/L. Harvesting the microalgae may include exposing the microalgae to a second stress level. The second stress level may include a combination of light, additional CO2, and a chemical trigger that includes nitrogen, ammonium, ammonium nitrate, ammonium acetate, calcium carbonate and zinc (e.g., 0.3% nitrogen, 0.5% ammonia, 0.3% ammonium nitrate, 0.5% ammonium acetate, a 30% increase in calcium carbonate and 1% zinc).

Harvesting the microalgae may further include inducing gelification of the algae and separating the gelled algae from the liquid medium. Gelification may include injecting chilled $CO_2$ into the liquid medium. Microalgae may be harvested continuously, semi-continuously, or in a batch. The rate of harvesting the microalgae may be substantially equal to a rate of growing the microalgae. Lipid may be extracted by introducing super-critical carbon dioxide to the gelled algae. In some embodiments, extracting lipid may include separating the lipid layer from algae or algae debris. In other embodiments, lipid may be extracted by rupturing the microalgae using a laser or microwaves.

In one aspect, the system for culturing a microalgae biofamily includes an enclosed pond containing microalgae in growth medium and having a sloped bottom, at least one photobioreactor positioned above the pond, and a pump circulating the microalgae-containing growth medium between the pond at the at least one photobioreactor. The pump may be configured to circulate the microalgae containing growth medium multiple times per day (e.g., at least two times per day or at least six times per day). In another embodiment, the pump may be configured to circulate the microalgae containing growth medium at a rate equal to the maximum absorptive ability of the algae strains and their mutants. In certain embodiments, the sloped bottom of the pond is configured to induce the flow of the microalgae-containing growth medium from a high elevation to a low elevation. The pump may be positioned at the low elevation of the pond. In addition, the sloped bottom may be configured to further induce turbulence in the microalgae-containing growth medium.

In some embodiments, the system may further include a piping header having a fluid inlet and a fluid outlet, each being fluidically connected to the pond. In other embodiments, the system may further include a water treatment plant fluidically connected to a second fluid inlet of the piping header, a carbon dioxide supply fluidically connected to injection ports of the piping header and/or a harvester.

In certain embodiments, the system may further include a piping header having a fluid inlet fluidically connected to the pond and a fluid outlet fluidically connected to the harvester.

In some embodiments, the system may also include a carbon dioxide supply fluidically connected to injection ports of the piping header. Further, the piping header may comprise light emitting diodes.

In another aspect, the invention is directed to a method for building a microalgae biofamily for lipid production, the method comprising the steps of: (a) selecting at least two foundational microalgae species (e.g., *Anabaena* sp. and *Nostoc* sp.) and culturing the species in a liquid medium; and (b) maintaining culture conditions in the liquid medium for at least 30 days to cause formation of a mucilage or mantle structure (e.g., thereby enhancing cell size), said culture conditions comprising at least temperature, salinity, light exposure, and a nutrient level (e.g., one or more of the following: $KNO_3$, $K_2HPO_4$, $CaCl_2$, $MgSO_4$, ferric citrate, citric acid, $CoCl_2$, $H_3BO_3$, $MnCl_2$, $ZnSO_4$, $CuSO_4$, $Na_2MoO_4$, various silica, nitrogen, phosphorous pentoxide, potassium oxide, magnesium oxide, sulfur trioxide, calcium oxide, boron, iron, and zinc).

In certain embodiments, the method further comprises the step of: (c) following step (b), inoculating the liquid medium with a first plurality of additional microalgae species different from the at least two foundational species, and increasing a nutrient level in the liquid medium and modifying a photoperiod to which the microalgae species are exposed.

In certain embodiments, the method further comprises the step of: (d) following step (b) [or following step (c)], inoculating the liquid medium with a [second] plurality of microalgae species different from the at least two foundational species, and allowing at least one of the [second] plurality of species to join the mucilage or mantle structure (e.g., showing association of endogen reproductive cells).

In certain embodiments, the method further comprises the step of: (e) maintaining culture conditions for a period of time (e.g., at least 5 or 6 months) sufficient to grow the microalgae species and produce a medium having at least 30 g/L biomass content (e.g., 36 g/L).

This method may further comprise the step of: (f) following step (e), harvesting between about 1.2 and about 2.5 g/L biomass per day. Step (f) may comprise injecting an amount of the culture (in the liquid medium) into a carbon dioxide digester and exposing the culture to an abrupt pH level change to induce gelification of the culture (e.g., such that the culture contains about 2-3% water and/or such that increased efficiency of cell rupture and/or triglyceride separation from the mucilage/mantle is achieved).

In certain embodiments, at least one step of the method takes place using an embodiment of the combined enclosed pond/photobioreactor system described herein.

The description of elements of the embodiments of one aspect of the invention may be applied in one or more additional aspects of the invention as well.

BRIEF DESCRIPTION OF THE DRAWINGS

The foregoing will be more readily understood from the following detailed description, in particular, when taken in conjunction with the drawings, wherein.

DETAILED DESCRIPTION

1. Multi-species Microalgae Biofamily

Figure 1:
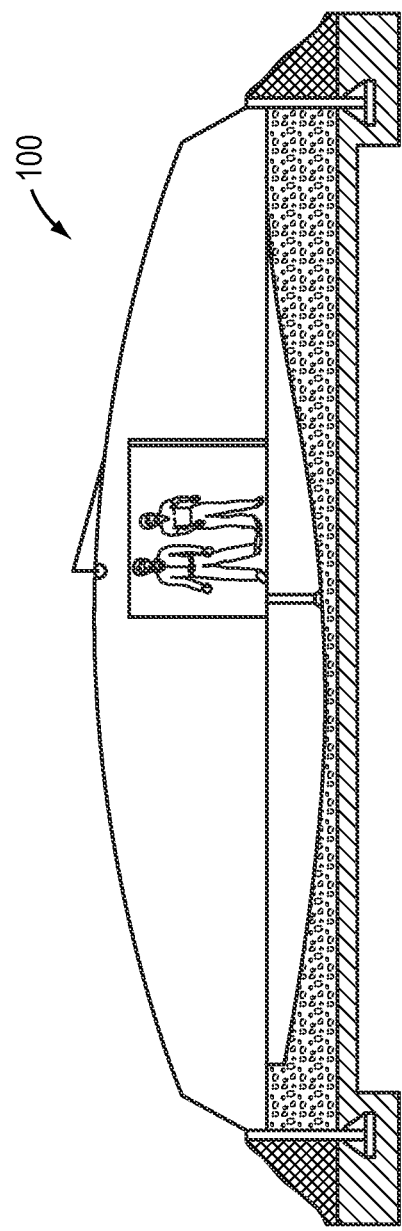
FIG. 1 is schematic drawings depicting a microalgae culture system including a closed pond and photobioreactors in accordance with various embodiments.

The term microalgae, as used herein, includes plankton (e.g., phytoplankton (e.g., cyanobacteria, diatoms and dinoflagellates), zooplankton, and bacterioplankton), microalgae (e.g., autotrophic microalgae, heterotrophic microalgae, and eukaryotic microalgae), macroalgae, other bacteria, fungi (e.g., yeast), and genetically modified cyanobacteria, microalgae, macroalgae, bacteria and/or fungi. Microalgae cultures may also include viruses, enzymes, and/or plants that may be included or added to the microalgae culture for increased lipid production.

Microalgae cultures as disclosed herein generally include two or more cyanobacteria or other algal species, at least some of which are in symbiotic relationship with each other. The two or more species form a multi-species microalgae biofamily with symbiotic relations and interdependencies among the various species. The species may include (but are not limited to) any combination of the following: *Euglena* sp. (*gracilis*), *Anabaena* sp. (e.g., *Anabaena variabilis, cylindrica, hassali,* and/or *planctonica*) and/or mutants thereof (e.g., AnaPat 368, AnaPat485, AnaPat324), AaronPat099 and/or AaronPat 0997, Biejclinc 4222, *Achananthes orientalis, Amphora* (e.g., *Amphora delicatissima* or *cafeiformis*), *Ankistnodesmus falcatus, Calothrix* (e.g., *Calothrix confervicola* and/or *crustacea*), *Chaetoceros* sp. (e.g., *Chaetoceros muelleri, gracilis,* and/or *muelleri subsalsum*), *Chaetomorpha linum, Clorococcum* sp., *Chlorrella* sp. (e.g., *Chlorrella ellipsoidea, Chlorrella pyrenoidosa,* and/or *Chlorrella salina*), *Chromonas* sp., *Chroococcus Turgidus, Chrysosphaera* sp., *Coelastrum* sp., *Calothrix crustacea, Cricophaera* sp., *Cryptomonas* sp., *Cyclotella* sp. (e.g., *Cyclotella meneghiniana* and/or *cryptica*), *Dermocarpa olivaceus, Dunaliella* sp. (e.g., *Dunaliella salina, bardawil,* and/or *tertioleta*), *Euglena viridis,* Fabilez 0093, *Navicula* sp. *Amphiprora hyalina, Eustigmatophyte flagellate, Pleurochysis* sp., *Franceia* sp., *Gleocapsa* sp., *Gloeothamnion* sp., *Hydrocoleum* (e.g., *Hydrocoleum lyngbyaceium* and/or *holdenii*), *Hymenomonas* sp., *Isochrysis aff. Galbana, Microcoleus chthonoplastes, Microcoleus tenerrimus, Monoraphidium* sp., *Nannochloropsis* sp. (e.g., *Nannochloropsis salina*), *Navicula* (e.g., *Navicula saprophil, pseudotenelloides, biskanterae, acceptata, saprophila,* and/or *pseudotenelloides*), *Nephrochloris* sp., *Nitzschia* sp. (e.g., *Nitzschia pusilla monoensis, elliptica, alexandrina, quadrangula, pusila monoensis, inconspicua, microcephala, frustulum, hantzchianna, intermedia, frustulum,* and/or *communis*), *Nodularia harveyana, Nostoc* sp., *Ochromonas* sp., *Oocystis* sp. (e.g., *Oocystis pusilla*), *Oscillatoria* sp. (e.g., *corallinae, subborevis, limnetica,* and/or *limosa*), *Pediastrum* sp. (e.g., *Pediastrum clarthatum*), *Phaeodactylum tricornutum, Platymonas* sp., *Pleurochrysis* sp. (e.g., *Pleurochrysis dentate*), *Prymnesiophyte* sp., *Pseudoanabaena* sp., *Pyraminonas* sp., *Rivularia nitida, Schizothrix cacicota, Siderocelis* sp., *Spirulina* sp. (e.g., *Spirulina platensis* and/or *Spirulina maxima*), *Stichococcus* sp., *Synechococcus* sp., *Tetraselmis suecica, Thalassiosira weissflogii, Tolypothrix lanata, Volvox aurex,* and/or YagoPat 077 and/or YagoPat 079. The biofamily may include mutants of any of the species disclosed herein, which mutants may be at least 98%, at least 95%, at least 90%, at least 85%, at least 80%, at least 75%, at least 70%, at least 65%, at least 60%, at least 55%, or at least 50% homologous with the corresponding wild-type species. The biofamily may, for example, include at least five, at least ten, at least twelve, or at least eighteen different species.

The various microalgae may contribute to the biofamily in different ways. For example, some of the algae may primarily serve as oil producers, and others may provide resistance to predatory species, bacteria, viruses and/or opportunistic bugs, and/or prevent population crash as well as facilitate nutrient and/or light uptake. In one preferred embodiment, the biofamily includes an *Anabaena* sp. and a *Nostoc* sp. These two species may, for instance, be found in Patagonian fresh waters (in the southern region of South America), and serve as foundational species for the biofamily.

In certain embodiments, a microalgae biofamily may comprise *Anabena* sp., *Nostoc* sp, *Oscilatoria limosa, Tolypothrix lanata, Calothrix crustacea, Chroococcus, Coelastrum, Pediastrum, Siderocelis, Volvox aureux, Euglena viridis,* and *Microcoleus tenerrimus.* In some embodiments, the microalgae biofamily may further comprise *Oscillatoria corallinae, Dunaliella salina, Chlorella salina, Chlorella pyrenoidosa, Spirulina platensis,* and/or *Spirulina maxima.*

In some embodiments, the microalgae biofamily may comprise an *Anabena, Nostoc, Oscilatoria limosa, Tolypothrix lanata, Calothrix crustacea, Chroococcus, Coelastrum, Pediastrum, Siderocelis, Volvox aureux, Euglena viridis, Microcoleus tenerrimus, Oscillatoria corallinae, Dunaliella salina, Chlorella salina, Chlorella pyrenoidosa, Spirulina platensis,* and *Spirulina maxima.*

In another embodiment, the biofamily includes *Hydrocoleum lyngbyaceum, Hydrocoleum hodenii, Nodularia hareyana, Microcoleus chthonoplastes, Rivularia nitida, Chaetomorpha linum, Calothrix confervicola, Calothrix crustacean, Oscillatoria subuliformis, Oscillatoria* sp., *Anabaena* sp. *Dermocarpa olivaceius, Schizothrix cacicola,* and optionally further species. These microalgae may be obtained from sea water around Cape Cod in Massachusetts. In certain embodiments, the biofamily includes seawater microalgae isolated from the ocean at depths exceeding 3 meters, where the temperature ranges from about −4 to about 20 degrees C.

The invention also provides a method for building a multi-species microalgae biofamily. The steps for building a microalgae biofamily include (a) selecting at least two foundational microalgae species, for example, *Anabaena* sp. and *Nostoc* sp.; (b) adding additional microalgae species that confer resistance to predator species, bacterial, and viruses; and (c) culturing the microalgae species selected in steps (a) and (b) in liquid medium. In some embodiments, at least one deep water algae species may be included in the biofamily. The deep water algae species may be adapted to grow a certain temperature, light intensity, nutrient source, and salinity (i.e., a first temperature, first light intensity, first nutrient source, and/or first salinity). When cultured, as part of a biofamily such as those disclosed herein, under different temperature, light, nutrient and salinity (i.e., a second temperature, second light intensity, second nutrient source, and/or second salinity), the deep water algae species may grow faster and/or produce more lipids and/or different lipid chains. In some embodiments, a second light intensity may be at least two-fold, at least 5-fold, or at least 10-fold higher than the first light intensity. A second temperature may be at least 5 degrees Celsius, at least 10 degrees Celsius, or at least 15 degrees Celsius higher than the first temperature. In some embodiments, the biofamily may be cultured under conditions including various micronutrients including, for example, $KNO_3$, $K_2HPO_4$, $CaCl_2$, $MgSO_4$, ferric citrate, citric acid, $CoCl_2$, $H_3BO_3$, $MnCl_2$, $ZnSO_4$, $CuSO_4$, $Na_2MoO_4$, various silica, nitrogen, phosphorous pentoxide, potassium oxide, magnesium oxide, sulfur trioxide, calcium oxide, boron, iron, and zinc.

2. Microalgae Culture System

In some embodiments, microalgae biofamilies as disclosed above are cultured in a closed-loop system combining a closed pond, one or more photobioreactors, and preferably a $CO_2$ header. FIG. 1 illustrates an exemplary system 100. The pond typically has horizontal dimensions in the range from a few feet to a few hundred feet, and a depth on the order of a few feet. For example, in one embodiment, the pond is 90 feet long, 45 feet wide, 4.5 feet deep at the deepest point, and holds a volume of culture medium (i.e., water containing microalgae and various nutrients) of about 136,000 gallons (or about 178,000 gallons including the pond, PBR(s), and any associated piping). In typical embodiments, the pond is fully enclosed by a cover or roof (e.g., a dome-shaped cover, rectangular cover or triangular cover), which may be made, for example, of glass or of a high-quality thermal plastic such as plexiglass and other specialized materials appropriate to the climate and target growth conditions (e.g., UV resistant and/or light filtering plastics). The temperature and humidity in and above the pond (underneath the covering) may be controlled through appropriate venting, and/or with additional equipment such as heaters, chillers, humidifiers/dehumidifiers, and/or a solar/thermal source, a ground source, a water source, heat pumps and/or waste heat from cogeneration or other thermal process. For example, radiant tubing may be installed at the bottom of the pond. In some embodiments, the pond is located adjacent to a natural water body that serves as a both a heat source and sink, providing low-cost means for heating or cooling the pond by using a heat pump or exchanger to transfer heat from that water body to the pond or vice versa, as the season and ambient temperature require. Alternatively or additionally, waste heat from other subsystems of the microalgae oil production facility may be recovered and used to heat the pond or drive a refrigeration cycle, allowing further energy savings.

The pond may have a sloped bottom, which causes the culture medium to flow from a high elevation (e.g., the shallow end of the pond) to a low elevation (e.g., the deep end of the pond) due to gravity, eliminating or at least reducing the need for pumps or paddles to establish flow inside the pond. Further, the curvature profile of the bottom may be designed to induce turbulence in, and thus thorough mixing of, the medium, which may reduce microalgae settling by transporting sinking microalgae back to the surface. The pond may include a divider or partition to create a high elevation and a low elevation within the pond. Liquid medium in the pond may flow from a high elevation to a low elevation by gravity without use of a pump or paddle to induce flow. In some embodiments, counterflow and flow from the roof can be used to provide additional turbulence and mixing, replicating natural conditions. At the deep end of the pond, the medium may be collected in a drain sump, and pumped to at least one photobioreactor, which are disposed adjacent to, e.g., above, the pond. From the photobioreactor(s), the medium flows by gravity back into the pond creating a siphon effect that substantially reduces overall pumping energy required for the system. The pump may be configured to cycle media through the pond/bioreactor systems multiple times per day. Further, the pump and drain sump may be configured to optimize the level of sedimentation in the pond. While a higher degree of sedimentation than found in prior-art ponds is desirable, some sediment may be beneficial as a nutrient for stimulating algae production. In certain embodiments, the system is designed and operated to reach sediment concentrations similar to those found in natural water columns.

The photobioreactors may be flat panels, and of rectangular shape. It is understood that the size and number of the photobioreactors (e.g., panels) can be scaled depending on the size of the pond, local growing conditions and space requirements or limitations. In some embodiments, where photoinhibition may be of concern, the panels may be limited and/or deployed sparingly or used with shading and vice versa where local solar incidence is low. The panels include translucent tubing, typically between about 1 mm to about 20 cm in diameter (e.g., from about 1 mm to about 10 cm in diameter, about 1 mm to about 5 cm in diameter, about 1 mm to about 1 cm in diameter, or about 5 mm to about 1 cm in diameter), which may be arranged in a meander-like fashion in a translucent housing. In some embodiments, the housing is made of glass that is textured so as to enhance the scattering and concentration of light into the tubing. Materials that may be used for the tubing and/or housing are well-known in the art.

In operation, the algae-containing medium flows through the tubing, where it is exposed to light from the sun or external artificial light sources. To increase the overall energy efficiency of the system, any artificial light sources used may be directly or indirectly solar-powered. For example, a battery may be charged during day times via solar cells, and then serve as an energy supply for lamps, LEDs, or other light sources that are capable of providing light exposure at any time. To prevent the formation of an algae film on the interior tubing wall, internal wipers may be included in the tubing. For example, o-ring-shaped wipers may be operated with an automated push-pull system to periodically clean the tubing. In certain embodiments, the photobioreactors further include internal light sources, such as arrays of LEDs that may be affixed to the tubing to provide supplemental, year-round light leveling. LEDs may also be used to expose the microalgae to selected wavelengths, which may be advantageous for algae growth. In some embodiments, the photobioreactors further include light sensors, which may be used to automate control of the LEDs and/or other artificial light sources based on the diurnal cycle. The photobioreactor panels may be arranged in a tiled fashion on the pond cover, and may shade the pond. In some embodiments, microalgae in the pond experience night-like lighting conditions, whereas microalgae in the photobioreactors experience day-like lighting. By pumping the algae-containing medium periodically through the pond and photobioreactors, a night-day cycle may be simulated. It is contemplated herein that the size and number of the photobioreactors may be scaled according to the size of the pond to control (e.g., maximize) cycling of the algae-containing medium between the pond and the photobioreactors appropriate to the species and local ambient conditions as they impact design requirements and targets. In certain embodiments, the flow of the microalgae culture from the pond to the photobioreactor(s) back to the pond is continuous to control the amount of light exposure and nutrients provided to the cells.

Figure 2:
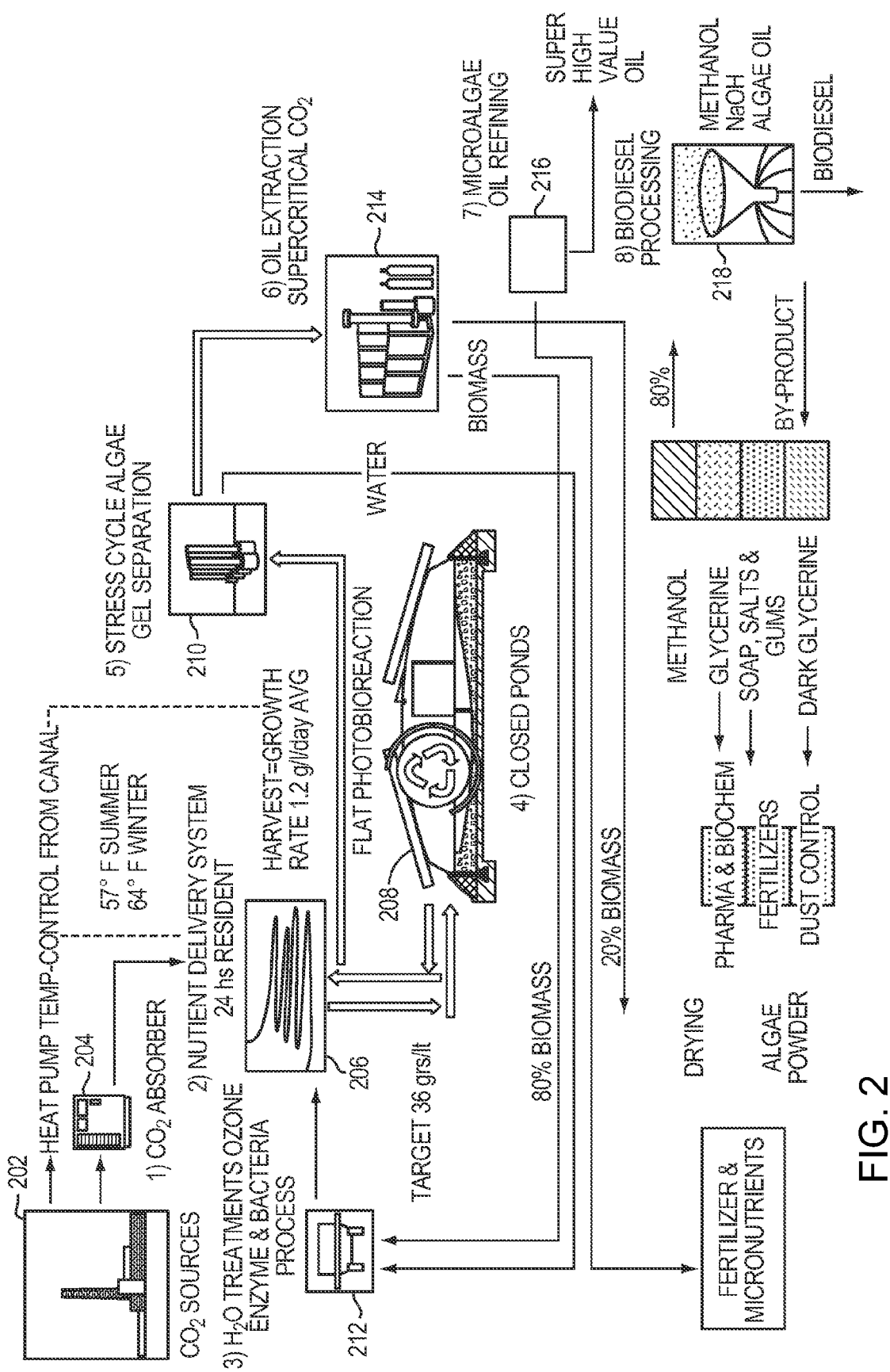
FIG. 2 is a schematic diagram illustrating an integrated system for culturing and producing oil from microalgae in accordance with various embodiments.

The system 100 depicted in FIG. 1 may be integrated with a $CO_2$ supply, environmental control functionality, and/or equipment for harvesting the microalgae and extracting and purifying oil, as illustrated schematically in FIG. 2. In this exemplary integrated system 200, $CO_2$ is captured from industrial exhaust stacks 202, using a $CO_2$ absorber system 204. Flue gas may be delivered to the absorber system 204 via air-cooled piping that substantially lowers the temperature of the gas before the gas enters a sealed chamber, in which it may be further cooled by water spray. The cooled gas then passes through a crush-shell filter for particulate filtering, acid neutralization and, if necessary, heavy metal removal. Filtered gas continues to a storage cylinder for load leveling and back-up.

A $CO_2$ delivery system serves to deliver $CO_2$ from the storage cylinder to the microalgae culture. The delivery system may comprise one or more $CO_2$ piping headers 206 having a pipe diameter of, e.g., two inches, and additional piping that connects the header to the pond/photobioreactor system 208. In some embodiments, two piping headers 206 are used, which can alternatively operate as a feed cycle, in which the algae undergo normal growth, or as a harvest cycle. The exit of the two headers "Y" so that the direction of algae culture flow can be controlled automatically to return to the ponds or sent to harvest. The headers 206 may be interconnected to provide redundancy in case of the failure of one or the other.

During the feed cycle, algae-containing medium is continuously cycled through the first $CO_2$ header, which primarily serves to deliver nutrients and $CO_2$ to the algae culture. Filtered gas is injected into the header 206 at distributed injection points and at a rate that may be continuously adjusted to the rate of $CO_2$ uptake by the algae. This uptake rate may vary depending on, e.g., the algae growth cycle, the temperature of the medium, nutrient availability, lighting conditions, or a combination thereof. In certain embodiments, 0.8 kg of $CO_2$ are provided for each kg of algal biomass (see Table 1). The exposure to $CO_2$ and proscribed nutrients and growth conditions leads to a gradual and continuous stressing of the algae, resulting in increased lipid production. Because the introduction of $CO_2$, if not compensated for, would increase the acidity of the medium, calcium carbonate ($CaCO_3$) may also be injected as needed to balance the pH. Typically, the pH of the medium is held in a range between 6.5 and 8.5. The amount of $CaCO_3$ required to balance the pH is determined experimentally, and depends on the specific composition of the medium, particularly the amount of dissolved oxygen, nitrogen oxide and sulfur oxide, and the biological activity of the microalgae.

In addition to $CO_2$ and $CaCO_3$, a nutrient mixture that contributes to the stressing may be injected. In some embodiments, the nutrient mixture includes nitrogen (in an amount that results in a concentration of about 0.3% in the medium), ammonium (in an amount that results in a concentration of about 0.5% in the medium), ammonium nitrate (in an amount that results in a concentration of about 0.3% in the medium, and ammonium acetate (in an amount that results in a concentration of about 0.5% in the medium) as exemplified in Table 1. The temperature of the culture medium is, in typical embodiments, about 15° C. during the normal growth phase. The pipes of the header 206 may be opaque to expose the algae to darkness, or translucent to allow for light penetration, depending on the algae species and desired growth conditions. In some embodiments, LEDs are implemented into the header 206 to facilitate control over the light level that the algae are exposed to.

TABLE 1

Stress Profile for Microalgae Species

| Compound | Normal Growth Level | Harvest Stress Level |
|---|---|---|
| Nitrogen | 0.3% | 0.3% |
| Ammonium | 0.5% | 0.5% |
| Ammonium Nitrate | 0.3% | 0.3% |
| Ammonium Acetate | 0.5% | 0.5% |
| Zinc | — | 0.1% |
| $CaCO_3$ | maintain pH @6.5-8.5 | 30% increase due to CO2 increase to maintain pH @6.5-8.5 |
| $CO_2$ | 0.8 kg/kg biomass | 1 kg/kg 8° C. |

TABLE 1-continued

Stress Profile for Microalgae Species

The algae culture may be monitored with physical sensors (measuring temperature, pressure, etc.) and periodic lab analysis of the chemical composition of the pond medium. The algae concentration is usually in the range from about 20 g/l to about 50 g/l. Preferably, algae are allowed to grow to and are maintained at a concentration of about 36 g/l. Concentrations above that threshold may be harvested (e.g., continuously, semi-continuously, or in batch). The timing and amount of algae to be harvested are determined based on the algae growth rate and lipid profile and/or the sensor and lab data collected during algae culturing.

Harvesting involves, first, separating a portion of the algae from the pond (e.g., concentrations above 36 g/l) and introducing them into the second $CO_2$ header 206, through which they are cycled at a rate such that the residence time for algae within the header 206 is about twenty-four hours. In the second $CO_2$ header, the algae are exposed to a second stress level (e.g., a higher stress level) based on a combination of light, additional $CO_2$ (increased to a about 1 kg per kg biomass), and a chemical trigger. The injected $CO_2$ preferably has a temperature of 8° C. (e.g., chilled $CO_2$). Light is provided by green, blue, and yellow LEDs or others as appropriate to the strain mix and desired lipids. The chemical trigger may be injected near the inlet of the second $CO_2$ header. The chemical trigger may include the same nutrients that were provided in the feed cycle, e.g., nitrogen, ammonium, ammonium nitrate, ammonium acetate, and calcium carbonate, and, in addition, zinc (for example, in Table 1, compare "Normal Growth Level" column with "Harvest Stress Level" column). In some embodiments, the nitrogen-containing compounds may be supplied at the concentration as in the feed cycle, and zinc may be supplied in an amount resulting in a concentration of about 0.1% in the medium. In general, however, the concentrations may depend on the initial lipid profile. To balance the pH (which would otherwise decrease due to the increased $CO_2$ concentration), an increased amount of $CaCO_3$ (30% higher than in the pond and feed cycle) may be injected through ports along the second $CO_2$ header. As a result, the pH in the second $CO_2$ header is maintained in the range from about 6.5 to about 8.5.

The increased stress level in the second $CO_2$ header results in the conversion of lipids contained in the algae (which include essential oils) to other, more desirable lipids and/or fatty acids. The oil may be of high quality and/or purity, and may include or consist essentially of fatty acid methyl acids (e.g., methyl tetradecanoate, methyl pentadecanoate, methyl hexadecanoate, methyl heptadecanoate, methyl octadecanoate, and/or methyl eicosanoate). Carbon chain lengths of most of the compounds may vary from 14 carbons with zero double bonds to 22 carbons with zero double bonds. Some traces of fatty acids containing short chains or unusually long chains and multiple unsaturated bonds (e.g., fatty acids containing 20 carbons and five double bonds) may also be included. In an exemplary embodiment, the composition of the resulting oil is illustrated in the gas chromatogram shown in FIG. 3.

In addition to inducing lipid conversion, the injection of chilled $CO_2$ may also further stimulate the algae to gel, which simplifies the subsequent physical separation of the oils from the remaining biomass (e.g., algae debris). The stressed and gelled algae may be harvested at a harvest port that may be integrated into the return loop from the pond system 208 to the header 206. In general, algae may be harvested continuously, semi-continuously, or in a batch process. Preferably, algae are withdrawn at the harvest port at a rate that is continuously matched to the algae growth rate, facilitating a continuous production process. In preferred embodiments, the algae concentration in the growth medium is maintained at about 36 grams per liter, which has been found to provide an optimized combination of a high algae growth rate and a low susceptibility to population crash or invasion. Harvested algae are sent to a harvester 210, where the gelification may continue, as described in more detail below. The gelled algae can easily be separated from the liquid medium, which is then returned to the $CO_2$ header 206 and ultimately the ponds, after passing through a water treatment facility 212.

The water treatment facility 112 serves as the point of entry for all water used for algae culture in the system, including raw seawater and recycled water from the harvest as well as from the oil extraction process. Water is sterilized with ozone, high-intensity ultraviolet light, and through enzymatic and bacterial processes as known in the art. Following sterilization, the water may be inoculated with algae. The water treatment facility may further serve to nutrify the water and to control the water chemistry to optimize it as a growth medium for the algae.

The harvested and gelled algae are pumped to an oil extraction facility 214, e.g., a supercritical $CO_2$ extractor. There, the cell walls are ruptured, thereby releasing the oil, which is subsequently separated from the remaining plant matter. The extracted plant matter may be dried for use in fish farming, nutriceuticals, cosmetics, or fertilizer. Alternatively, it may be sent through the water treatment facility 212 and returned to the pond/photobioreactor system 208. In certain embodiments, about 80% of the biomass is recycled into the system, whereas the remaining 20% are dried and utilized for other purposes.

The algae oil is typically already highly purified in the extraction process. To further increase its quality, a secondary purification step may be carried out in an oil refinery 216. In this process, undesirable free fatty acids are converted, and the oil is filtered using methods well-known in the art. Typically, the purification is associated with a minor loss of material, which may be recaptured as fertilizer and/or micronutrients. The refined oil may then be converted to biodiesel in a biodiesel processor 218 or sent to a refining process that may include hydrotreating or fracturing of the oil for desired petroleum substitutes such as biojet fuel, bioaviation fuel, biogasoline and other bio-derived petrochemical feedstock substitutes. The processor 218 includes a high-velocity vortex cone (rotating, e.g., at about 1200 rpm), in which the algae oil reacts with methanol and sodium hydroxide to form biodiesel. For example, for one 100 kg of oil, about 13 liters of methanol and 1.8 kg of sodium hydroxide are consumed. Excess methanol may be recycled. The produced biodiesel may have ASTM or EN quality (e.g., ASTM D-6751 (USA); EN 14214 (Europe); ON C1191 (Austria); CSN 65 6507 (Czech Republic); Journal Officiel (France); DIN V51606 (Germany); UNI10635 (Italy); and SS 155436 (Sweden)). By-products of the process may be recovered for pharmaceutical and biochemical uses, fertilizer and soap production, and/or dust control.

3. Methods for Culturing Microalgae and Increasing Oil Production

Various embodiments relate to culturing methods that optimize various environmental parameters, such as, e.g., light exposure, temperature, and/or $CO_2$ and nutrient availability, to achieve increased algae growth and/or oil production. The systems 100, 200 described above are particularly suited for controlling environmental parameters in accordance with these methods. However, various features of the methods may also be implemented in other algae culture systems, including conventional ponds and bioreactors.

In certain embodiments, the algae are cultured in brackish water. For the purpose of this disclosure, brackish water is salt water with a salinity of between 1% and 50%, preferably between 25% and 40%, and most preferably about 33% of the salinity of seawater. Brackish water has been observed to have a high resistance to contamination and to result in high algae growth rates and oil producing performance. Brackish water may be obtained by establishing chemical conditions into pure seawater that lower the salinity. Alternatively, brackish water may be directly taken from, e.g., Wellfleet Harbor on Cape Cod or similar low salinity estuaries, which have a salt concentration of around 33% that of pure seawater. As the entire system is a closed loop environment, once system fill is achieved, a very low water make-up is required.

Certain microalgae species are preferably cultured at temperatures between about 14° C. and about 18° C. Deep water species, which are exposed to lower temperatures in their natural environment, tend to produce more oil when placed in a warmer environment. In some embodiments, algae (e.g., deep water algae) are cultured at a temperature that is at least 5° C. higher than the temperature of the water from which the algae have been isolated. Further, the algae in culture may be exposed to higher (e.g., tenfold higher) light intensities than they are in their natural environment.

Algae culturing typically involves supplying nutrients to algae. Such nutrients may include dewatered sewage sludge, fish waste (e.g., striped bass waste), processed bivalve (e.g., oyster, clam, and scallop) shells. Further, the culture medium may include calcium carbonate and micronutrients, i.e., minerals, vitamins, and trace elements (such as, e.g., $KNO_3$, $K_2HPO_4$, $CaCl_2$, $MgSO_4$, ferric citrate, citric acid, $CoCl_2$, $H_3BO_3$, $MnCl_2$, $ZnSO_4$, $CuSO_4$, $Na_2MoO_4$, and various silica). In certain embodiments, the concentrations of the micronutrients vary between seasons. Table 2 provides exemplary micronutrient profiles for spring, summer, fall, and winter by the listing the respective concentrations of nitrogen, phosphorous pentoxide, potassium oxide, magnesium oxide, sulfur trioxide, calcium oxide, boron, iron, and zinc.

TABLE 2

Exemplary Micronutrient Profiles by Season

| Season | Spring | Summer | Fall | Winter |
|---|---|---|---|---|
| Nitrogen (N) total | 12% | 20% | 15% | 12% |
| Nitric acid | 5.5% | 9.5% | 7% | 5.5% |
| Ammonia | 6.5% | 10.5% | 8% | 6.5% |
| $P_2O_5$ | | | | |
| soluble in water and citrate ammonia neutral | 12% | 5% | 5% | 10% |
| Soluble in Water | 6% | 2.5% | 2.5% | 7% |
| Potassium oxide ($K_2O$) soluble in water and coming from sulfate | 17% | 10% | 20% | 20% |
| Magnesium oxide (MgO) total | 2% | 3% | 2% | 2% |
| Soluble in water | 1.6% | 2% | 1.4% | 1.6% |

TABLE 2-continued

Exemplary Micronutrient Profiles by Season

| Season | Spring | Summer | Fall | Winter |
|---|---|---|---|---|
| Sulfur trioxide ($SO_3$) total | 15% | 7.5% | 20% | 20% |
| Soluble in water | 12% | 6% | 16% | 16% |
| Calcium oxide (CaO) total | 5% | 3% | 2% | 2.5% |
| Boron (B) total | 0.02% | — | 0.02% | 0.02% |
| Iron (Fe) total | — | 0.3% | — | — |
| Zinc (Zn) total | 0.01% | — | 0.01% | — |

In various embodiments, the microalgae are exposed to light-dark cycles whose period is shorter than one day. For example, the algae may be cycled through a pond and a series of photobioreactors multiple times a day. In some embodiments, algae may be cycled from the deep end of a pond (e.g., where there is no or minimal light exposure) to at least one photobioreactor, which may be exposed to natural levels of sunlight, artificially concentrated sunlight, or light from artificial sources, such as LEDs. Without wishing to be bound by theory, algae biomass production is predominantly autophototrophic (i.e., photosynthetic) in light periods, and heterotrophic in dark periods. Thus, this accelerated change in light exposure between the pond and at least one photobioreactor may cause increased overall algae production per day. Depending on the scaling of the pond and photobioreactors, algae may be cycled between the pond and at least one photobioreactor, e.g., at least once, twice, three times, four times, five times, six times, ten times, fifteen times, or twenty times a day to increase the number of light-dark cycles per day. In certain embodiments, six light-dark cycles per day have been found to maximize algae growth.

4. Methods for Microalgae Harvesting and Oil Extraction

Figure 4:
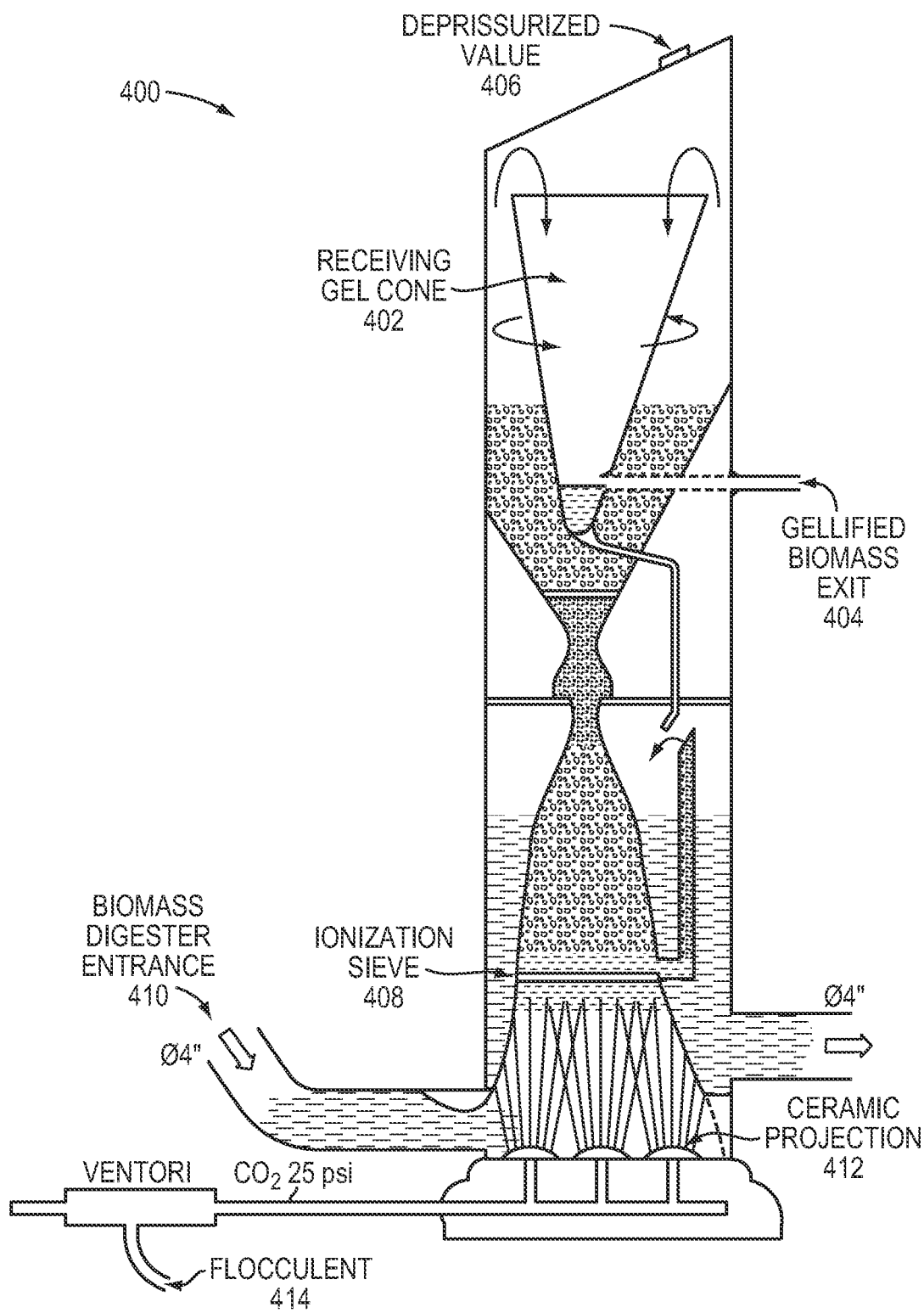
FIG. 4 is a schematic drawing illustrating a gelification apparatus in accordance with various embodiments.

Various embodiments relate to the harvesting of microalgae by inducing their gelification, which allows for easy separation of the algal biomass from the culture medium. Gelification may be carried out in a $CO_2$ header 206, or in a separate harvester 210, which includes one or more columns through which the algae-containing medium is pumped upwards. An example of such a harvester 210 is illustrated in FIG. 4 as schematic system 400, featuring a receiving gel cone 402, a gellified biomass exit 404, a depressurized valve 406, an ionization sieve 408, a biomass digester entrance 410, a ceramic projector 412, and flocculent conduit 414. Carbon dioxide, which may be introduced into the flow in the header 206, is exposed to an ascending pressure in the column(s) by introduction of additional $CO_2$ bubbles from the absorber 204 and/or by a system of specially designed nozzles through which the medium passes. Further, a flocculent may be injected into the medium. Together with the trigger compound, chilled CO2, the calcium carbonate, the flocculent and induced microbubbles causes the algae to further gel and condense. Since water, calcium carbonate, and biomass have different specific weight, they may be separated based on their location in the column: the gelled algae tend to float on the water. Sieves may serve to siphon off the biomass concentrate, which is then received in a cone where it is pumped to the extractor. The water content of the biomass may thus be reduced to about 2-3% without the use of centrifuges or drying.

The biomass is sent to the extractor 214, where it may be combined with supercritical $CO_2$ (e.g., $CO_2$ with a temperature and pressure above its critical temperature and pressure, which has both fluid and gas properties, rendering it very suitable as a solvent). This process extracts intracellular, intercellular and extracellular oil from the algae and the intercolony mantle. While conventional systems require a temperature of about 95 degrees C. and a pressure of about 70 psi to break the cell walls, the gelification of the algae reduces the required temperature to about 80 degrees C. and the pressure to about 40 psi, resulting in significant energy savings. The lipids dissolve in the supercritical $CO_2$, permitting mechanical separation of the lipid layer from the remaining plant matter (e.g., algae or algae debris). Once the plant matter is removed, the $CO_2$ is allowed to off-gas and led back into the $CO_2$ feed system, leaving behind oil of high purity. This process is advantageous in that it does not require the use of hazardous chemicals.

An alternative process for extracting oil from the microalgae involves rupturing the cell walls using a laser or microwaves. In this method, the gelled biomass is circulated through a cylindrical tube at a speed depending on the tube size and algal mass density (e.g., continuously, semi-continuously, or in a batch). In one embodiment, laser light, e.g., from a sieve-ray laser source, is directed into the tube, whose inner surface is polished and reflective, causing scattering and distribution of the light throughout the volume of the tube. The laser frequency is in the ultraviolet, visible, or infrared regime. The laser beam power is sufficiently high to completely rupture the cell walls and membranes, but sufficiently low to be non-ionizing and, thus, not to alter the triglycerides and lipid content. In some embodiments, a pulsed laser (e.g., a Q-switched laser) with pulse energies in the range from about 1 millijoule to several hundreds of millijoules is used.

EXAMPLES

The invention is further illustrated by the following examples. The examples are provided for illustrative purposes only, and are not to be construed as limiting the scope or content of the invention in any way.

Example 1

Determination of Fatty Acid and Sterol Composition

Microalgae were cultured and harvested, and lipids were extracted as described herein. The fatty acid composition, sterol composition, acidity, iodine index, and phosphorous content was determined on a microalgae oil sample. Acidity was determined using a Norma IRAM 5512; phosphorous content in parts per million (ppm) was determined using AOCS Ca 12-55; iodine index was determined using a Norma IRAM 5512; sterol composition was determined using a Norma IRAM 5660; and fatty acid composition was determined by gas chromatography using a Norma IRAM 5651.

Acidity, determined as a gram per 100 g expressed like oleic acid, was 0.50; iodine was 123.3; and no phosphorous was detected in the sample (see Appendix A).

The composition of fatty acids was determined by gas-liquid chromatography of fatty acid methyl esters. The results shown in Table 3 are expressed in grams fatty acid per 100 grams of methyl ester.

TABLE 3

| Fatty Acid Composition | |
|---|---|
| Fatty Acid | Microalgae Oil |
| C14:0 myristoic acid | 0.8 |
| C14:1 tetradecenoic acid | 0.1 |
| C15:0 pentadecanoic acid | 0.1 |
| C16:0 hexadecanoic acid | 10.3 |

TABLE 3-continued

Fatty Acid Composition

| Fatty Acid | Microalgae Oil |
|---|---|
| C16:1 hexadecenoic acid | 1.4 |
| C17:0 margaric acid | 0.2 |
| C17:1 heptadecenoic acid | 0.1 |
| C18:0 stearic acid | 3.7 |
| C18:1 octadecenoic acid | 26.0 |
| C18:2 trans-octadecadienoic acid | 0.5 |
| C18:2 octadecadienoic acid | 47.0 |
| C18:3 octadecatrienoic acid-ω3 | 0.6 |
| C18:4 octadecatetraenoic acid-ω3 | 0.2 |
| C20:0 arachadonic acid | 0.4 |
| C20:1 eicosenoic acid | 1.3 |
| C20:4 eicosatetraenoic acid-ω6 | 0.3 |
| C20:4 eicosatetraenoic acid-ω3 | 0.2 |
| C20:5 eicosapentenoic acid-ω3 | 1.0 |
| C22:0 docosanoic acid | 0.6 |
| C22:1 docosenoic acid | 0.8 |
| C24:1 tetracosenoic acid | 0.3 |
| C22:3 docosatrienoic acid | 0.1 |
| C22:4 docosatetraenoic acid | 0.1 |
| C22:5 docosapentenoic acid-ω6 | 0.2 |
| C22:5 docosapentenoic acid-ω3 | 0.5 |
| C22:6 docosahexenoic acid-ω3 | 3.2 |

The composition of sterols was also determined. The results shown in Table 4 are expressed in grams per 100 grams of total sterols. (See Appendix A).

TABLE 4

Sterol Composition

| Sterol | Microalgae Oil |
|---|---|
| Cholesterol | 30.2 |
| Campesterol | 8.8 |
| Campestanol | 0.6 |
| Stigmasterol | 7.1 |
| Not identified | 1.5 |
| Clerosterol | 0.5 |
| β-Sitoesterol | 42.6 |
| Δ5-Avenasterol | 3.6 |
| Δ7-Estigmasterol | 3.5 |
| Δ7-Avensterol | 1.6 |

Example 2

Biodiesel Analysis

Microalgae were cultured and harvested, and lipids (oil) were extracted and converted into biodiesel (also referred to herein as algadiesel) as described herein. An algae biodiesel (B100) sample was analyzed for cloud point, flammability, water content, viscosity, density, acid number and iodine value. The results of this analysis are presented in Table 5.

TABLE 5

Algadiesel Analysis

| | | |
|---|---|---|
| Cloud Point | −12° C./10° F. | report |
| Flammability | 52.9-53° C./127.4° F. | report (greater than 120° F. desirable) |
| Water Content | 0.05% | max 0.05% (Europe 0.075%) |
| Viscosity @40 deg C. | 3.736 cst | 1.9-6 (diesel typical 2-4) |
| Density @15 deg C. | 0.895 | report |
| Acid Number | 0.2 | max 0.5 mg/g |
| Iodine Value | 32.5 | max 120 (lower the better) |

The cloud point values presented in Table 5 can be compared to cloud point values for #2 diesel (without additives) (e.g., −10° C./15° F.), soy (e.g., 2° C./35.6° F.), and canola (e.g., −2° C./28.4° F.).

Example 3

Biodiesel Analysis by Two-Dimensional Gas Chromatography with Flame Ionization Detection A microalgae biodiesel (B100) sample was obtained following harvesting, gelification, extraction, and conversion into biodiesel as described herein. Based on visual inspection, the B100 sample was light yellow, free of particulates, and had a viscosity typical of petroleum diesel and on the low end of typical biodiesel samples.

Figure 3:
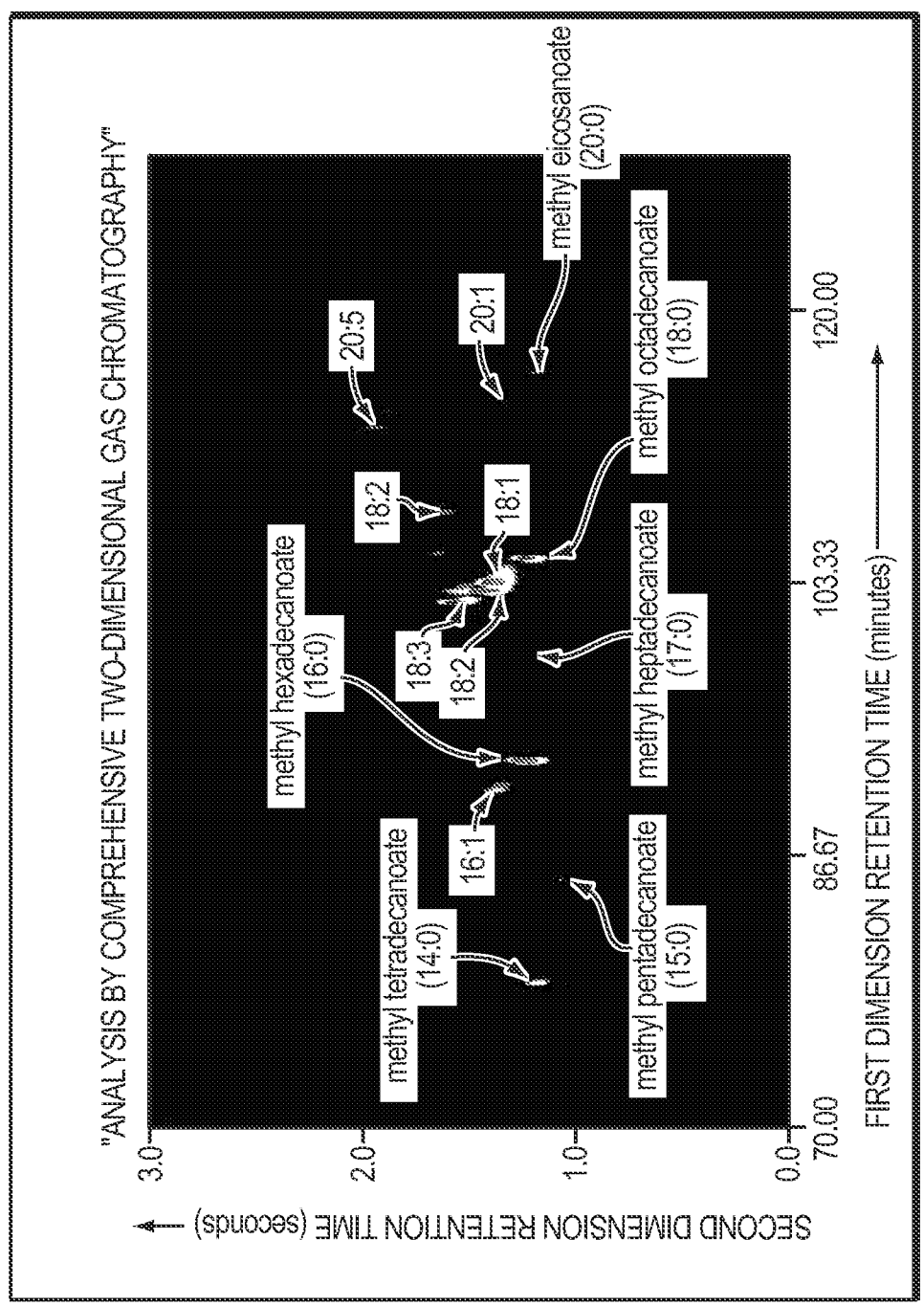
FIG. 3 is a gas chromatogram illustrating the composition of oil produced from microalgae in accordance with one embodiment.

To determine the composition and the purity of the microalgae biodiesel B100 sample, it was analyzed by two-dimensional gas chromatography with flame ionization detection (GC×GC-FID) (see, e.g., DeMello, J. A. et al. (2007) "Biodegradation and environmental behavior of biodiesel mixtures in the sea: An initial study," *Marine Pollution Bulletin* 54:894-904.) GC×GC-FID analysis indicated that the B100 sample was composed of a suite of fatty acid methyl esters (FAMEs) with carbon chain lengths from 14 carbons with zero double bonds (labeled 14:0) to 22 carbons with zero double bonds (22:0) as shown in FIG. 3. The analysis also indicated that the sample was at least 99% FAMEs with no impurities. In addition, some trace FAMEs were detected including one with 20 carbons and five double bonds (10:5), which is consistent from algal-derived biodiesel (and not that from land-based plants or seed). The sample was characterized as a high quality biodiesel sample.

Example 4

Radiocarbon Analysis of Biodiesel Sample

The microalgae biodiesel sample (B100) was also analyzed using radiocarbon-dating (see, e.g., Reddy, C. M. et al. (2008) "Determination of biodiesel blending percentages using natural abundance radiocarbon analysis: Testing the accuracy of retail biodiesel blends," *Env. Sci. and Technol.* 42:2476-2482). Radiocarbon analysis can be used to differentiate fossil carbon, which has no detectable radiocarbon, from modern or contemporary carbon, which can be detected by accelerator mass spectrometry. Radiocarbon analysis indicated the B100 sample was grown on a modern carbon dioxide source, which is consistent with algal-grown biodiesel.

Example 5

Lipid Production and Culture Profiles

Table 6, which summarizes 10 years of research and development, illustrates the effect of different culture conditions, including the type of system used, the facility description, the ambient temperature, composition of the growth medium, and the number of species, on the gross weight of dry biomass produced as well as on the relative content of lipids, proteins, and carbohydrates. In addition, the cellular wet biomass growth was 2.6 g/L for the year 8, 0.43 g/L for the year 9, and 1.8 g/L for year 10. The following abbreviations found in Table 6 are as follows:

OP: Open Pond;
CPGHT: Cover Pond Green House Type;
CPSCT: Cover Pond Commercial Scale Type;

CO2 T1: CO2 Natural;
CO2T2: CO2 from Fermentation;
CO2T3: Mineral/Industrial;
PTBR STD: Model 1 Used;
PBRT STD2: Model 2 Used;
PTBR STD 3: Model 3 Used;
BlindPTBR: Optical fiber & harvest column;
LED: Artificial photosynthetic period;
LZSKPTBR: Flat PTBR lizard skin;
PSW: Pure Sea Water;
MSW 1: Modified Sea Water;
FMSWF: Final Formula Modified Sea Water;
MCh: Medium Change;
FLC: Floculants;
CNTR: Centrifugal+Hexane;
ULT: UltraSoud;
GP+SPC: Gelly Point+Supercritical 1;
CHR: Chemical Rupture; and
DSC02: Digestor System of C02.

Example 6

Generation of a Multi-Species Biofamily

The multi-species biofamilies described in Table 6 include two foundational species, *Anabaena* sp. and *Nostocs* sp. We have observed that these two species predominate within the digestive tracts of bivalves in oceanic zones where the continental waters show significant differences in salinity and pH levels. These two species have also been observed as emerging in the marine bed of continental subterranean waters which represent big areas of conductivity stratification, temperature and cloudiness, together with high speeds and wide inter-tide ranges (12/14n and 8/10mt). The *Anabaena* sp. and *Nostocs* sp. may be found on scallops (able to feed at different depths) as well as on stationary bivalves such as oysters, geo ducks and mussels.

In our studies, we have simulated an environment influenced by two types of currents: one very warm and other very cold (e.g., the warm Canarias current, also called Brazilian warm current, and the cold Antarctic current), which forces these species to undergo morphologic changes together with slight cellular mutations. We have shown that these two species predominate in both summer and winter culture conditions with high temperature variations and big photoperiods according to the quantity of individual species, including at different depths (from 2 to 21mts).

In subsequent studies, the two foundational species were sowed in a culture system such as the pond and photobioreactor culture system described herein for 30 to 45 days under temperature, salinity, light and nutrient conditions designated in Table 6. At this stage, the culture conditions contained minimal nitrates.

Both species were quick to colonize at all stages of the system and were moved weekly in the PBRs. The combination of these two species in a close circuit with no competence of any kind triggered an increase in size, specifically at the bottom of the ponds, where the movement of the water is small. This situation stimulates de stratification of the culture from the bottom of the pond. Basically these species induced colonization of the entire circuit (even with independence of $CO_2$, light and nitrates conditions).

The most visible interaction of *Nostoc* and *Anabaena* is the formation and combination of several groups of spherical cells (typical in these two species) that begin to create a mantle or mucilage over the surfaces where the cells increase in size and broaden their cellular membrane.

After about 45 days, the biofamily was inoculated with the following species: *Oscillatoria limosa, Tolypothrix lanata, Calotrix crustácea* and *Chrococcus turgidus*. At the same time, the nutrients were increased and the photoperiod was modified to 14:10 (from a photoperiod of 16:8—exposure of the foundational species). The biofamily typically reached equilibrium approximately 60 days after the incorporation of these four additional species observing that the inoculated culture had a weighted growth rate of the combined culture (e.g., the foundational plus the four additional species) at approximately 30 days. This reflects a 150 times (+/−10) more cells in the beginning, having started in all groups from a 4×10$^5$ and with irradiance levels from 90 μmol m$^{-2}$s$^{-1}$ at the beginning, increased up to 138 μmol m$^{-2}$s$^{-1}$.

The mucilage or mantle structure that bounds and covers the different colonies is related to its own synthesis. The different colonies at the proximity of the membrane start to produce the mucilage and expel it, building a continuous agglutinant layer as a permanent growth. At maximum points of stress (e.g., prior to harvesting lipids), the mucilage structure contains significant amounts of triglycerides that the different species contained in the mucilage accumulated during stress.

After approximately 100 to 110 days of interaction of the six species, the biofamily was inoculated with the following additional species: *Coelastrum* sp, *Pediastrum clarthatum*, and *Siderocelis* sp. After approximately twelve days, the *Coelastrum* Sp and *Siderocelis* sp., started to create colonies that joined the mucilage or mantle that bound them. For example, 2-4-8 cells were observed inside the same cellular wall, which represented essentially a transition or association of the endogen reproductive cells. *Pediastrum* was determined to be an essential part of the recirculation system because it helps recirculation from the bottom of the pond to the surface.

After approximately six months, the biofamily reached equilibrium and attained a resident biomass of about 36 grams per liter. Approximately, 1.2 to 2.5 grams per liter per day of biomass were harvested with the following weighted media of the three associated organisms that reached at maximum stress (48 to 56 hours prior to harvesting) and produced up to 60% of triglycerides: 20-22% intracellular, 5-8% at the mucilage expelling process and 30-35% extracellularly in the mantle.

At the end of this period, the photoperiod conditions were sustained permanently and independently of the natural photoperiod, e.g., in 12:12 of approximately the 80% of the culture medium (the total volume of water involved in our system. 80% of the culture medium in circulation and light exposure was injected into the $CO_2$ digester system, between 70-80% of the resident biomass in artificial photosynthesis conditions, with metabolism variable rates of around 60-80%. The radiation in this period is over the 260 μmol m$^{-2}$s$^{-1}$ throughout 12 hours, performed by Lutron Lx101 sensors. The remaining $CO_2$ in the digester circuit is withdrawn and slightly refrigerated before injection into the harvesting unit together with the micro-air bubbles. The $CO_2$, together with the hardening process and biomass agglutination of the biomass, exposed during the 10 final hours of permanence in the $CO_2$ digester system undergoes a sudden pH change that allows the biomass to reach a gelly point splitting it from the water and culture medium. The harvested $CO_2$ is obtained from the superior part of the harvester unit and compressed for such use.

An advantage of taking the almost gelly biomass to the supercritical state with 2-3% water is that it requires much less energy consumption. The cells, mucilage and mantle each contained high lipid concentrations. We observed increased efficiency in cell rupture and triglycerides separation from the mucilage and mantle due to specific weight differences.

TABLE 6

Example of Lipid Production and Culture Profiles

| Year | System Full Capacity & Culture Medium | Facility Description* see Codes below | Type of System Used & Harvest Gross Weight | Season | Culture Details | Species | Protein | Lipid | Carbohydrates |
|---|---|---|---|---|---|---|---|---|---|
| 1 | 20 M3 PSW | OP + C02T1 | Mch 78 kilos | August-March | 5 species 14° C. Avg. | Anabaena, Nostoc, Oscillatoria limosa, Tolypothrix lanata, Calothrix crustacea | 51-56 | | |
| 2 | 40 M3 PSW | OP + C02T2 PTBR STD | FLC 236 kilos | August-December | 7 species 15° C. Avg | Anabaena, Nostoc, Oscillatoria limosa, Tolypothrix lanata, Calothrix crustacea, Chroococcus, Coelastrum | 54-56 | 6-10 | 10-18 |
| 3 | 60 M3 PSW | CPGHT + C02T2 + PBRT STD2 | CNTR 721 kilos | February-December | 9 species 16° C. | Anabaena, Nostoc, Oscillatoria limosa, Tolypothrix lanata, Calothrix crustacea, Chroococcus, Coelastrum, Pediastrum, Siderocelis | 58-61 | 15-19 | 14-18 |
| 4 | 80M3 MSW 1 | CPGHT + C02T2 + PBRT STD2 | CNTR 3,890 kilos | January-January | 10 species 16° C. | Anabaena, Nostoc, Oscillatoria limosa, Tolypothrix lanata, Calothrix crustacea, Chroococcus, Coelastrum, Pediastrum, Siderocelis, Volvox aureux | | 17-21 | 12-17 |
| 5 | 80M3 MSW 1 | CPGHT + C02T2 + blind PTBR | ULT 1.126 kilos | April-November | 12 species 18° C. | Anabaena, Nostoc, Oscillatoria limosa, Tolypothrix lanata, Calothrix crustacea, Chroococcus, Coelastrum, Pediastrum, Siderocelis, Volvox aureux, Euglena viridis, Microcoleus tenerrimus | | 36-43 | 48-53 |
| 6 | 40M3 MSW 1 | CPGHT + C02T2 + DSC02 blind PTBR | ULT + GP 1,675 kilos | January-January | 12 species 16° C. | Anabaena, Nostoc, Oscillatoria limosa, Tolypothrix lanata, Calothrix crustacea, Chroococcus, Coelastrum, Pediastrum, Siderocelis, Volvox aureux, Euglena viridis, Microcoleus tenerrimus | | 52-57 | 33-40 |
| 7 | 80M3 FMSWF | CPGHT + C02T3 + DSC02 Blind PTBR | GP + CHR 4,200 kilos | February-February | 12 species 14° C. | Anabaena, Nostoc, Oscilatoria limosa, Tolypothrix lanata, Calothrix crustacea, Chroococcus, Coelastrum, Pediastrum, Siderocelis, Volvox aureux, Euglena viridis, Microcoleus tenerrimus | | 55-58 | 30-36 |
| 8 | 220 M3 FMSWF | CPSCT + C02T3 + DSC02 Blind PTBR + PTBR STD 3 + LED | GP + SPC 6,890 kilos | April-February | 14 species 16° C. | Anabaena, Nostoc, Oscillatoria limosa, Tolypothrix lanata, Calothrix crustacea, Chroococcus, Coelastrum, Pediastrum, Siderocelis, Volvox aureux Euglena viridis, Microcoleus tenerrimus, Oscillatoria corallinae, Dunaliella salina | | 56-60 | 33-39 |
| 9 | 220 M3 FMSWF | CPSCT + C02T3 + DSC02 + PTBR STD 3 + LED | GP + SPC 3,120 kilos | April 2007 April 2008 | 16 species 18° C. | Anabaena, Nostoc, Oscillatoria limosa, Tolypothrix lanata, Calothrix crustacea, Chroococcus, Coelastrum, Pediastrum, Siderocelis, Volvox aureux, Euglena viridis, Microcoleus tenerrimus, Oscillatoria corallinae, Dunaliella salina, Chlorella salina, Chlorella pyrenoidosa | | 56-64 | 33-37 |
| 10 | 5 M3 FMSWF | Close Tank + LZSKPTBR | SPC 470 kilos | March-January | 18 species 16° C. | Anabaena, Nostoc, Oscillatoria limosa, Tolypothrix lanata, Calothrix crustacea, Chroococcus, Coelastrum, Pediastrum, Siderocelis, Volvox aureux, Euglena viridis, Microcoleus tenerrimus, Oscillatoria corallinae, Dunaliella salina, Chlorella salina, Chlorella pyrenoidosa, Spirulina platensis, Spirulina maxima | | 58-65 | 54-64 |

While the invention has been particularly shown and described with reference to specific preferred embodiments, it should be understood by those skilled in the art that various changes in form and detail may be made therein without departing from the spirit and scope of the invention as defined by the appended claims.

Incorporation by Reference

The entire disclosure of each of the patent documents and scientific articles cited herein is incorporated by reference for all purposes.

What is claimed is:

1. A method for building a microalgae biofamily for lipid production, the method comprising the steps of:

(a) culturing a culture comprising a mixture of *Anabaena* and *Nostoc* optionally in combination with one or more of *Oscillatoria limosa*, *Tolypothrix lanata*, and *Calothrix crustacea* in a culture medium wherein the culture medium is pure sea water;

(b) controlling culture conditions for at least 30 days to cause formation of a mucilage or mantle structure, said culture conditions comprising at least temperature, salinity, light exposure, and a nutrient level comprising at least one member selected from the group consisting of: $KNO_3$, $K_2HPO_4$, $CaCl_2$, $MgSO_4$, ferric citrate, citric acid, $CoCl_2$, $H_3BO_3$, $MnCl_2$, $ZnSO_4$, $CuSO_4$, $Na_2MoO_4$, various silica, nitrogen, phosphorous pentoxide, potassium oxide, magnesium oxide, sulfur trioxide, calcium oxide, boron, iron, and zinc;

c) thereafter adding *Chroococcus* and *Coelastrum*; and thereafter d) adding a plurality of micro algae species comprising *Pediastrum*, and *Siderocelis* and culturing the mixture for a time sufficient for at least one of said *Pdiasturum* or *Siderocelis* species to join the mucilage, and thereafter e) adding *Volvox aureux, Euglena viridis*, and *Microcoleus tenerrimus*, and continuing cultivation for a period long enough to achieve a biomass of at least 30 g/l while bringing the salinity of the water into the range 25-50% that of seawater, and allowing at least one of the plurality of species to join the mucilage or mantle structure.

2. The method of claim 1, wherein step (c) comprises increasing a nutrient level in the liquid medium and modifying a photoperiod to which the microalgae species are exposed.

3. The method of claim 1, further comprising the step of:
(f) maintaining culture conditions for at least 5 months sufficient to grow the microalgae species and produce a medium having at least 30 g/l biomass content.

4. The method of claim 3, further comprising the step of:
(g) following step (f), harvesting between about 1.2 and about 2.5 g/l biomass per day.

5. The method of claim 4, wherein step (g) comprises injecting an amount of the culture into a carbon dioxide digester and exposing the culture to an abrupt pH level change to induce gelification of the culture such that the culture contains about 2-3% water and/or such that increased efficiency of cell rupture and/or triglyceride separation from the mucilage/mantle is achieved.

6. The method of claim 1 wherein after step (e) microalgae species comprising *Oscillatoria corallinae, Dunaliella salina, Chlorella salina, Chlorella pyrenoidosa, Spirulina platensis*, and *Spirulina maxima* are added to the mixture and the salinity of the mixture is further reduced.

7. The method of claim 1 wherein step (e) is carried out for at least five months.

* * * * *